(12) United States Patent
Beck et al.

(10) Patent No.: US 8,752,436 B2
(45) Date of Patent: Jun. 17, 2014

(54) PRESSURE SENSOR SEAL AND METHOD OF USE

(75) Inventors: Kent Beck, Salt Lake City, UT (US); Philip Eggers, Cottonwood Heights, UT (US)

(73) Assignee: Zevex, Inc., Salt Lake City, UT (US)

( * ) Notice: Subject to any disclaimer, the term of this patent is extended or adjusted under 35 U.S.C. 154(b) by 285 days.

(21) Appl. No.: 13/248,931

(22) Filed: Sep. 29, 2011

(65) Prior Publication Data

US 2012/0079886 A1    Apr. 5, 2012

Related U.S. Application Data

(60) Provisional application No. 61/388,883, filed on Oct. 1, 2010.

(51) Int. Cl.
*G01L 7/00* (2006.01)
*A61M 1/00* (2006.01)

(52) U.S. Cl.
USPC .............................. 73/756; 604/506

(58) Field of Classification Search
None
See application file for complete search history.

(56) References Cited

U.S. PATENT DOCUMENTS

| | | |
|---|---|---|
| 2,899,907 A | 8/1959 | Becher |
| 3,209,596 A | 10/1965 | Kelly |
| 3,736,930 A | 6/1973 | Georgi |
| 3,768,934 A | 10/1973 | Magerle |
| 3,790,313 A | 2/1974 | Magerle |
| 3,978,731 A | 9/1976 | Reeder et al. |
| 4,187,057 A | 2/1980 | Xanthopoulos |
| 4,217,993 A | 8/1980 | Jess et al. |
| 4,229,299 A | 10/1980 | Savitz et al. |
| 4,244,365 A | 1/1981 | McGill et al. |
| 4,322,978 A | 4/1982 | Fromm |
| 4,322,979 A | 4/1982 | Fromm |
| 4,373,525 A | 2/1983 | Kobayashi |
| 4,447,191 A | 5/1984 | Bilstad et al. |
| 4,460,355 A | 7/1984 | Layman |
| 4,469,481 A | 9/1984 | Kobayashi |
| 4,498,843 A | 2/1985 | Schneider et al. |
| 4,529,401 A | 7/1985 | Leslie et al. |
| 4,554,837 A | 11/1985 | Danby et al. |

(Continued)

FOREIGN PATENT DOCUMENTS

| | | |
|---|---|---|
| DE | 2447005 | 10/1974 |
| DE | 20000965 U1 | 1/2000 |

(Continued)

OTHER PUBLICATIONS

The International Bureau of WIPO, International Preliminary Report on Patentability issued in International Application No. PCT/US2011/054047 Apr. 2, 2013.

(Continued)

*Primary Examiner* — Andre Allen
(74) *Attorney, Agent, or Firm* — Hodgson Russ LLP

(57) ABSTRACT

A pressure sensor and method of use provides for the detection of a sudden increase or decrease of pressure within tubing during the administration of solutions to a patient. Detection of an occlusion, partial or other significant pressure change in the tubing is accomplished by measuring the compression and/or expansion of the tubing. Transfer of the change in force within the tubing is communicated from the tubing to a sensor by a transfer rod which as a membrane attached thereto to provide a seal thereabout.

23 Claims, 6 Drawing Sheets

(56) References Cited

U.S. PATENT DOCUMENTS

| | | |
|---|---|---|
| 4,555,949 A | 12/1985 | Danby et al. |
| 4,559,034 A | 12/1985 | Kirita et al. |
| D284,221 S | 6/1986 | Kerkut |
| 4,601,700 A | 7/1986 | Thompson et al. |
| 4,612,810 A | 9/1986 | Martens |
| 4,624,413 A | 11/1986 | Corsette |
| 4,663,965 A | 5/1987 | Metcalf et al. |
| 4,762,518 A | 8/1988 | Kreinick |
| 4,784,576 A | 11/1988 | Bloom et al. |
| 4,784,577 A | 11/1988 | Ritson et al. |
| 4,850,807 A | 7/1989 | Frantz |
| 4,857,818 A | 8/1989 | Hobbs |
| 4,863,425 A | 9/1989 | Slate et al. |
| 4,882,575 A | 11/1989 | Kawahara |
| 4,884,013 A | 11/1989 | Jackson et al. |
| 4,910,682 A | 3/1990 | Wolff et al. |
| 4,913,703 A | 4/1990 | Pasqualucci |
| 4,919,650 A | 4/1990 | Feingold et al. |
| 4,950,244 A * | 8/1990 | Fellingham et al. .......... 604/118 |
| 4,973,309 A | 11/1990 | Sultan |
| 4,976,687 A | 12/1990 | Martin |
| 4,994,035 A | 2/1991 | Mokros |
| 5,008,556 A | 4/1991 | Mersch |
| 5,096,385 A | 3/1992 | Georgi et al. |
| 5,098,380 A | 3/1992 | Aizawa et al. |
| 5,098,384 A | 3/1992 | Abrams |
| 5,099,184 A | 3/1992 | Hornung et al. |
| 5,181,912 A | 1/1993 | Hammett |
| 5,195,960 A | 3/1993 | Hossain et al. |
| 5,201,711 A | 4/1993 | Pasqualucci |
| 5,244,463 A | 9/1993 | Cordner, Jr. et al. |
| 5,254,992 A | 10/1993 | Keen et al. |
| 5,279,556 A | 1/1994 | Goi et al. |
| 5,312,334 A | 5/1994 | Hara et al. |
| 5,346,477 A | 9/1994 | Edwards et al. |
| 5,355,735 A | 10/1994 | Miller et al. |
| 5,370,612 A | 12/1994 | Maeda et al. |
| 5,395,320 A | 3/1995 | Padda et al. |
| D357,312 S | 4/1995 | Riquier et al. |
| 5,438,868 A | 8/1995 | Holden et al. |
| 5,482,446 A | 1/1996 | Williamson et al. |
| 5,514,102 A | 5/1996 | Winterer et al. |
| 5,531,680 A | 7/1996 | Dumas et al. |
| 5,538,405 A | 7/1996 | Patno et al. |
| D374,718 S | 10/1996 | Dodge et al. |
| 5,575,631 A | 11/1996 | Jester |
| 5,614,677 A | 3/1997 | Wamsiedler et al. |
| 5,630,710 A | 5/1997 | Tune et al. |
| 5,657,000 A | 8/1997 | Ellingboe |
| 5,683,233 A | 11/1997 | Moubayed et al. |
| D388,876 S | 1/1998 | Sampson |
| D389,228 S | 1/1998 | Winterer et al. |
| 5,704,584 A | 1/1998 | Winterer et al. |
| 5,720,721 A | 2/1998 | Dumas et al. |
| 5,733,061 A | 3/1998 | Child |
| 5,741,216 A | 4/1998 | Hemmingsen et al. |
| 5,746,756 A | 5/1998 | Bromfield et al. |
| 5,789,675 A | 8/1998 | Blaine et al. |
| 5,791,881 A | 8/1998 | Moubayed et al. |
| 5,810,323 A | 9/1998 | Winterer et al. |
| 5,844,587 A | 12/1998 | Ando et al. |
| 5,860,938 A | 1/1999 | Lafontaine et al. |
| 5,924,852 A | 7/1999 | Moubayed et al. |
| 5,935,106 A | 8/1999 | Olsen |
| 5,964,377 A | 10/1999 | Demarest et al. |
| 5,983,725 A | 11/1999 | Fischer et al. |
| 5,984,149 A | 11/1999 | Thanisch et al. |
| 5,989,222 A | 11/1999 | Cole et al. |
| 5,996,650 A | 12/1999 | Phallen et al. |
| 6,017,326 A | 1/2000 | Pasqualucci |
| 6,023,970 A | 2/2000 | Blaine |
| 6,030,359 A | 2/2000 | Nowosielski |
| 6,116,472 A | 9/2000 | Wanbaugh et al. |
| 6,121,739 A | 9/2000 | Haberlander |
| 6,142,979 A | 11/2000 | McNally et al. |
| 6,164,921 A | 12/2000 | Moubayed et al. |
| 6,192,752 B1 | 2/2001 | Blaine |
| 6,261,262 B1 | 7/2001 | Briggs et al. |
| 6,328,720 B1 | 12/2001 | McNally et al. |
| D455,489 S | 4/2002 | Beck et al. |
| 6,371,732 B1 | 4/2002 | Moubayed et al. |
| 6,416,293 B1 | 7/2002 | Bouchard et al. |
| 6,463,813 B1 | 10/2002 | Gysling |
| 6,506,035 B1 | 1/2003 | Beck |
| 6,523,414 B1 | 2/2003 | Malmstrom et al. |
| 6,531,708 B1 | 3/2003 | Malmstrom et al. |
| 6,543,885 B2 | 4/2003 | Bahl et al. |
| 6,595,950 B1 | 7/2003 | Miles et al. |
| 6,623,447 B2 | 9/2003 | Miles et al. |
| 6,636,010 B1 | 10/2003 | Malmstrom et al. |
| 6,659,976 B2 | 12/2003 | Beck et al. |
| 6,682,500 B2 | 1/2004 | Soltanpour et al. |
| 6,685,670 B2 | 2/2004 | Miles et al. |
| 6,749,591 B1 | 6/2004 | McNally et al. |
| 6,750,468 B2 | 6/2004 | Malmstrom et al. |
| D501,924 S | 2/2005 | Cise et al. |
| 6,852,094 B2 | 2/2005 | Beck et al. |
| D503,799 S | 4/2005 | Beck |
| D503,978 S | 4/2005 | Beck |
| D504,506 S | 4/2005 | Beck et al. |
| D505,199 S | 5/2005 | Beck et al. |
| 6,902,541 B2 | 6/2005 | McNally et al. |
| 6,907,788 B2 | 6/2005 | Malmstrom et al. |
| D507,647 S | 7/2005 | Beck et al. |
| 6,923,785 B2 | 8/2005 | Miles et al. |
| 6,942,636 B2 | 9/2005 | Holst et al. |
| 6,979,311 B2 | 12/2005 | Miles et al. |
| D523,553 S | 6/2006 | Beck et al. |
| 7,070,575 B2 | 7/2006 | Beck et al. |
| 7,121,143 B2 | 10/2006 | Malmstrom et al. |
| 7,150,727 B2 | 12/2006 | Cise et al. |
| D536,783 S | 2/2007 | Cise et al. |
| 7,207,780 B2 | 4/2007 | Bach |
| 7,367,963 B2 | 5/2008 | Cise et al. |
| 7,530,968 B2 | 5/2009 | Gonnelli |
| 2002/0169424 A1 | 11/2002 | Miles et al. |
| 2004/0220542 A1 | 11/2004 | Cise et al. |
| 2005/0004540 A1 | 1/2005 | McNally |
| 2005/0096593 A1 | 5/2005 | Pope et al. |
| 2005/0119625 A1 | 6/2005 | Miles et al. |
| 2005/0209563 A1 | 9/2005 | Hopping et al. |
| 2005/0277912 A1 | 12/2005 | John |
| 2006/0058740 A1 | 3/2006 | Cise |
| 2006/0142692 A1 | 6/2006 | Jacobson et al. |
| 2006/0278001 A1 | 12/2006 | Kaneko et al. |
| 2007/0118078 A1 | 5/2007 | McNally |
| 2007/0151346 A1 | 7/2007 | Malmstrom et al. |
| 2007/0241917 A1 | 10/2007 | Tiwet et al. |
| 2008/0098798 A1 | 5/2008 | Riley |
| 2008/0103445 A1 | 5/2008 | Blaine et al. |
| 2008/0119782 A1 | 5/2008 | Steinman |
| 2008/0134750 A1 | 6/2008 | Riley |
| 2008/0208117 A1 | 8/2008 | Steinman |
| 2009/0049919 A1 | 2/2009 | Hills |
| 2009/0149801 A1 | 6/2009 | Crandall |
| 2009/0254034 A1 | 10/2009 | Beck |
| 2012/0078170 A1 * | 3/2012 | Smith et al. ............. 604/67 |
| 2012/0078181 A1 * | 3/2012 | Smith et al. ............. 604/152 |
| 2012/0078182 A1 * | 3/2012 | Smith et al. ............. 604/152 |
| 2012/0078183 A1 * | 3/2012 | Smith et al. ............. 604/152 |
| 2012/0078184 A1 * | 3/2012 | Smith et al. ............. 604/152 |
| 2012/0078185 A1 * | 3/2012 | Smith et al. ............. 604/152 |
| 2012/0078216 A1 * | 3/2012 | Smith et al. ............. 604/500 |
| 2012/0078217 A1 * | 3/2012 | Smith et al. ............. 604/500 |
| 2012/0078222 A1 * | 3/2012 | Smith et al. ............. 604/506 |

FOREIGN PATENT DOCUMENTS

| | | |
|---|---|---|
| EP | 0 261 860 | 3/1988 |
| EP | 0 410 187 | 1/1991 |
| GB | 2 338 759 | 12/1999 |

(56) References Cited

FOREIGN PATENT DOCUMENTS

| | | |
|---|---|---|
| JP | S56-31758 | 3/1981 |
| JP | S58-163860 | 10/1983 |
| JP | H02-01805 | 8/1990 |
| JP | 05-042219 | 2/1993 |
| JP | 10-048759 | 2/1998 |
| WO | WO 96/08666 | 3/1996 |
| WO | WO 98/04301 | 2/1998 |

OTHER PUBLICATIONS

WIPO, International Searching Authority ISA/KR, International Search Report issued Apr. 20, 2012 in International Application No. PCT/US2011/054047.

\* cited by examiner

PRESSURE SENSOR SEAL AND METHOD OF USE

RELATED APPLICATIONS

The present application claims the benefit of U.S. Provisional Patent Application Ser. No. 61/388,883, filed Oct. 1, 2010, which is incorporated herein by references in its entirety.

BACKGROUND OF THE INVENTION

1. The Field of the Invention

The present invention relates to an apparatus and method for detecting occlusions during delivery of a solution to a patient. More particularly, the present invention relates to a sensor having a flexible, waterproof barrier that may be used in connection with an infusion or feeding pump to prevent damage to the pump in the event of a fluid leak or spill.

2. State of the Art

Treating a patient often requires administering to the patient certain fluids, medication or other nutrients in solution form. The physical condition of a patient may require enteral feeding of a nutrient solution into a patient's stomach or bowel. Likewise, a patient may require parenteral or intravenous infusion of medication, hydration and/or nutrients.

In enteral feeding it is important to provide the solution, which can be somewhat viscous, within a desired pressure range to ensure the solution is delivered, but at a pressure which is not uncomfortable to the patient or which could damage tissue surrounding the outlet of the feeding set. While controlling pressure is a concern, medical personnel must also be concerned about possible occlusion of the feeding set which prevents delivery of the feeding solution. This can be caused by a blockage within the feeding tube as may be caused by materials in the feeding solution, or externally by the feeding set being crimped or otherwise obstructed by the patient or some other cause.

Likewise in parenteral and IV administration, it is important to deliver the solution accurately to the patient as the patient may require the medication, fluids or nutrition in the infused solution in order to survive. As with enteral feeding, the infusion of solutions parenterally should be done at a pressure low enough to avoid discomfort or damage to the veins, while at sufficient pressure to assure delivery of the solution. Likewise, it is also important to ensure that flow of the solution has not been occluded, as this may prevent the patient from receiving necessary hydration and medication for treating various conditions.

One method of delivering medications and other solutions is by using a feeding or infusion pump. (For ease of reference, both enteral feeding sets, parenteral feeding sets and IV infusion sets, and their associated pumps, are referred to herein as infusion pumps and infusion sets. Any use of "infusion pumps" and "infusion sets" shall be deemed to incorporate enteral, parenteral, and IV applications unless specifically noted to the contrary).

Infusion pumps are designed to deliver controlled doses to the patient, thus allowing medical personnel to monitor and control the amount of nutrition, hydration and/or medication which the patient is receiving. However, use of an infusion pump introduces risk that flow of a solution through the tubing may become impeded, resulting in the patient not receiving needed fluids and medications. For example, a patient may unintentionally roll onto the tubing thereby kinking or compressing the tubing and stopping or reducing the flow. Likewise a blood clot or other debris may block the flow of solution through the tubing.

To overcome these types of problems standard safety features on modern infusion sets include sensors to detect changes in flow of a solution through the tubing and to warn medical personnel when flow through the tubing is impeded. Some sensors on modern infusion sets detect occlusions by measuring a force exerted within the tubing of the infusion set. For example, if an occlusion occurs downstream of the infusion pump then the pressure inside the tubing downstream from the pumping mechanism will increase and the flexible tubing will expand. Expansion of the tubing exerts a force on the sensor that detects the increased pressure as a downstream occlusion. Alternatively, if an occlusion occurs upstream of the pumping mechanism, pressure inside the tubing (between the occlusion and the pumping mechanism) will generally decrease causing the flexible tubing to exert less force on the sensor than would normally be exerted when the infusion set is operating properly. This decrease in force will reduce the actual amount of solution which is being delivered to the patient and will be detected by the sensor as an upstream occlusion. If the pressure in the tubing falls outside of a predetermined range, the sensors will generally cause an alarm to sound indicating the presence of an occlusion. If the pressure changes do not fall outside the desired range, the pressure change may still be used to alter the cycles (typically either duration or frequency of cycles) of the pumping mechanism as the pressure has an effect on the amount of solution which is pumped during each cycle.

Another problem that medical personnel must be concerned with when delivering solutions to a patient using an infusion set is contamination or damage to the pumping mechanism. Although the tubing and cassette of an infusion set is discarded after use with a particular patient, the pump which drives the solution through the infusion set may be used with subsequent patients. While the outer surfaces of the infusion set can be easily sanitized with cleaning agents, it may difficult to clean the interior of the pump.

Likewise, while an infusion set is typically sealed, infusion pumps are used in a medical environment where solutions may be spilled on the pump. To prevent damage to the electronics of the pump, including the pressure sensors, a sealing mechanism is typically required.

To ensure that that the interior of the pump does not become contaminated and to prevent liquids from damaging the electronics, infusion sets often include seals that prevent liquid and bacteria from entering or exiting inner surfaces of the pump that are more difficult to routinely clean. To this end, the sensors (or external portions thereof) are often protected with a sheath of elastomeric material to prevent solution from contacting the sensor should a leak occur. This elastomeric material also provides a microbial barrier to make the pump easier to sanitize to ensure that cross-contamination does not occur with subsequent usage of the pump.

An example of such an elastomeric membrane disposed between the tubing and a rod associated with the sensor can be seen in U.S. Pat. No. 5,989,222. While the membrane helps to shield the rod from fluids, the elastomeric membrane also deforms somewhat under the changing pressuring in the tubing and thus may decrease the sensitivity of the sensor by absorbing all or some of the change in force exerted by the tubing.

Thus, there is a need for an improved sensor for detecting occlusions in an infusion set. The sensor's ability to detect a force exerted by the tubing of the infusion set should be maximized while providing a microbial barrier for patient protection and protecting the sensor from damage in the event a solution leaks from the infusion set or is otherwise spilled on the pump. It is also desirable to provide such a device which is relatively inexpensive and easy to use.

SUMMARY OF THE INVENTION

It is an object of the present to provide an occlusion sensor and method of use which substantially prevents contamination and/or damage to the sensor during administration of solutions to a patient.

According to one aspect of the present invention, an occlusion sensor may be disposed on a pump so as to be positioned along the infusion set. According to another aspect of the present invention, the occlusion sensor may include a transfer rod with a first end that selectively engages the tubing of an infusion set and a second end that engages a sensor and a sealing member disposed along the transfer rod.

According to another aspect of the present invention, the occlusion sensor may be disposed on an infusion set using a sealing membrane located between the first and second ends of the transfer rod, with the membrane extending around the circumference of the transfer rod.

According to yet another aspect of the present invention, the membrane may be a flexible, waterproof membrane that acts as a microbial barrier and seal around the transfer rod.

According to still another aspect of the present invention, the flexible, waterproof membrane may be preformed as part of an infusion pump.

In accordance with another aspect of the present invention, the transfer rod of the occlusion sensor may be attached to the infusion set by overlay molding an elastomeric material that adheres to the transfer rod and a plate that is attachable to an infusion pump.

In accordance with still another aspect of the present invention, the first end of the transfer rod may be in direct contact with the tubing of an infusion set and the second end of the transfer rod may be in direct contact with a sensor and includes a barrier that allows the plunger to move in response to pressure changes A change in pressure within the tubing of the infusion set may result in a change in force exerted by the tubing wall against the first end of the plunger, which is communicated to the sensor via the second end of the plunger.

These and other aspects of the present invention are realized in an occlusion sensor and method of use as shown and described in the following figures and related description.

BRIEF DESCRIPTION OF THE DRAWINGS

Various embodiments of the present invention are shown and described in reference to the numbered drawings wherein.

It will be appreciated that the drawings are illustrative and not limiting of the scope of the invention which is defined by the appended claims. The various elements of the invention accomplish various aspects and objects of the invention. It is appreciated that not every element of the invention can be clearly displayed in a single drawing, and as such not every drawing shows each element of the invention.

DETAILED DESCRIPTION

The drawings will now be discussed in reference to the numerals provided therein so as to enable one skilled in the art to practice the present invention. The drawings and descriptions are exemplary of various aspects of the invention and are not intended to narrow the scope of the appended claims.

Figure 1:
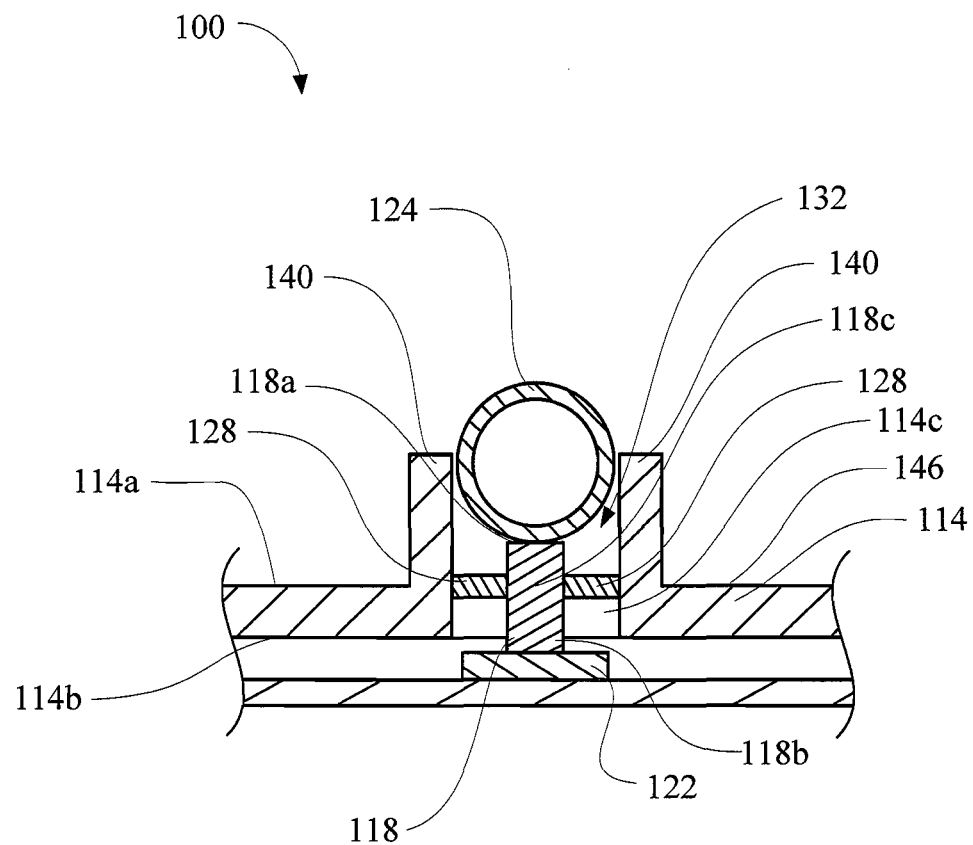
FIG. 1 shows a fragmented, cross-sectional side view of an occlusion sensor system made in accordance with the principles of the present invention.
Figure 1A:
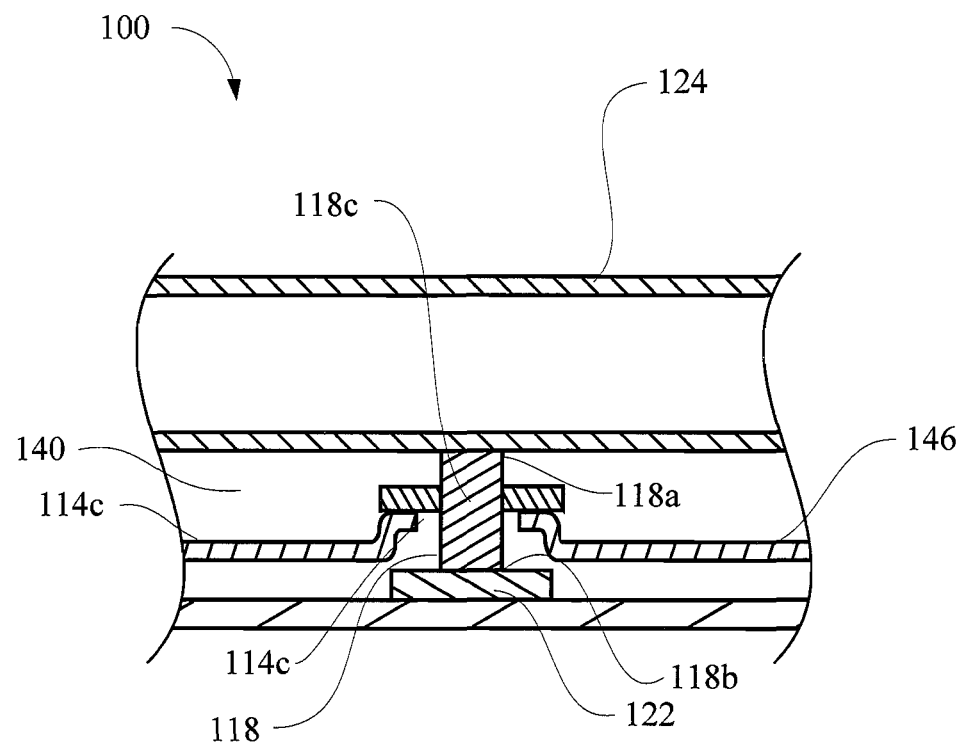
FIG. 1A shows a fragmented cross-sectional view of the occlusion sensor system of FIG. 1 taken lengthwise along the tubing of an infusion set.

Turning to FIGS. 1 and 1A, there are shown a fragmented, cross-sectional view of an occlusion sensor system, generally indicated at 100, according to principles of the present invention. FIG. 1 shows a cross-section taken perpendicular to the length of a tubing segment of an infusion set and FIG. 1A shows a cross-section of the same area taken along the length of the tubing of the infusion set.

The sensor system 100 is disposed on an infusion pump body 114 as may be used with an infusion set to deliver solution to a patient. It will be appreciated that the invention discussed herein could also be used with other types of pumps which are used to deliver liquids in other industries.

The sensor system 100 may include a transfer rod 118 disposed in a channel 132 formed by sidewalls 140. The channel 132 is typically disposed along a mounting plate 146. The mounting plate 146 is often formed at the top of the pump so that a top portion of the mounting plate is part of the outer surface 114 of the pump (which may be covered by a door) and the underside of the mounting plate 146 is part of the inner portion 114*b* of the pump. It will be appreciated that the mounting plate 146 may be integrally formed as part of the pump or may be a separate component that may be removably attached to a pump.

The transfer rod 118 typically extends through an opening 114*c* in the mounting plate 146 so that a first end 118*a* of transfer rod 118 is disposed in the channel 132 so as to contact the tubing 124 of an infusion set mounted on or adjacent the outer surface 114*a* of the pump body 114. A second end 118*b* of the transfer rod 118 may be disposed adjacent, and typically contacting, a sensor 122 disposed in the interior 114*b* of the pump body 114. The sensor 122 may be a piezoelectric transducer or other system which senses pressure in the tubing 124 via the transfer rod 118. Thus, as the tubing 124 expands or contracts, the transfer rod 118 will applying different amounts of force to the sensor 122. A pressure falling outside a predetermined range means either than an occlusion is present along the tubing 124 upstream from a pumping mechanism or that the tubing has not been properly loaded in the channel 132. Either way, this enables the pump to determine that an undesirable condition is present and an alarm may be sounded and the pump may shut down. A pressure rising outside a predetermined range indicates an occlusion downsteam which, if sufficient, may cause the pump to give an alarm and/or shut down.

In order to protect the sensor and other components within the pump body 114, it is important that fluids and/or other material which may potentially contaminate the pump not be allowed to enter the interior of the pump body. In prior pumps used in the medical industry, this may be done by placing a sheath or membrane above a rod or similar structure to form a seal such that the sheath or membrane is disposed between the rod and the tubing of an infusion set. Typically the sheath is elastomeric and can dampen the reactivity of the rod to the changes in pressure within the tubing. Thus, using a sheath or membrane as described in the prior art would likely reduces the sensitivity of a sensor in communication with the rod.

In accordance with the present invention, the occlusion sensor system 100 may use a flexible, waterproof membrane 128 which engages a central portion 118c of the transfer rod 118, i.e. between the first and second ends 118a and 118b, so that the first end 118a of the transfer rod 118 may directly contact the tubing 124 without having an elastomeric material disposed therebetween. The membrane 128 may also engage the pump body 114. For example, the membrane 128 may be attached to the sidewalls 140 of the channel 132 creating a microbial/contamination barrier, which may substantially prevent fluid and/or other materials from passing through opening 114c and damaging the sensor 122, and/or other internal parts of the pump.

The membrane 128 may be installed by overlay molding the membrane to a mounting plate 146 configured for receiving the transfer rod 118. The molded membrane 128 may act as a positioning member (both vertically and laterally) and a seal for the transfer rod 118. According to one aspect of the present invention, the membrane 128 may be comprised of a number of flexible materials, which are typically low durometer elastomers such as silicone and polyurethanes. One skilled in the art will appreciate that the membrane 128 can be comprised of any suitable material that acts as a microbial/contamination barrier and may be sufficiently flexible to allow the transfer rod 118 to communicate a force exerted on it by the tubing 124 to the sensor 122. It is also desirable, but not required, that the material bond to the body of the pump to provide a desirable seal.

It will be appreciated that while the transfer rod 118 can move, under normal conditions the movement of the transfer rod will typically be about 1 mm or less. Thus, the membrane 128 does not have to be highly flexible to avoid decreasing the amount of force transferred to the sensor 122.

When attached to the sidewalls 140, the membrane 128 may help maintain the position of the transfer rod 118 adjacent tubing 124 when the infusion set is in use to keep the transfer rod 118 in direct contact with tubing 124. Should an occlusion (partial occlusion, etc.) occur downstream from the pumping mechanism, pressure within the tubing 124 will increase, causing the tubing to expand. The expansion of tubing 124 creates a force that is exerted on the first end 118a of the transfer rod 118. The transfer rod 118 is typically substantially rigid and resists being compressed. Thus, the second end of the transfer rod 118 is able to communicate to the sensor 122 substantially all of a resulting force caused by a change in pressure inside tubing 124. This force may be detected as an occlusion and an alert may be sent to notify medical personnel of the occlusion.

Figure 2:
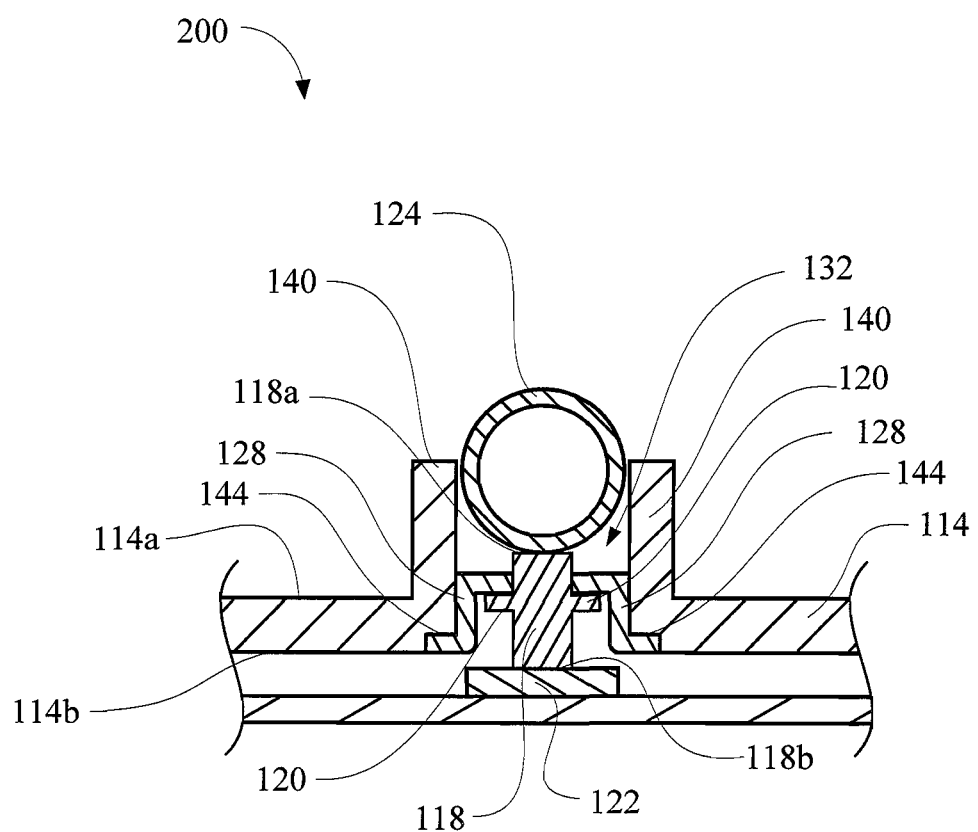
FIG. 2 shows a fragmented, cross-sectional side view of another occlusion sensor, made in accordance with the principles of the present invention, disposed on a pump body for an infusion set.

Referring now to FIG. 2, there is shown a fragmented, cross-sectional view of an alternate pressure/occlusion sensor system according to principles of the present invention, generally indicated at 200. The pressure/occlusion sensor system 200 is similar to the sensor system 100 seen in FIG. 2 above and has accordingly been labeled with corresponding reference numerals. The transfer rod 118 is disposed in the channel 132 and may include one or more flanges 120. Like the occlusion sensor system 100, the pressure/occlusion sensor system 200 may include a flexible, waterproof membrane 128 attached to the transfer rod 118. However, the membrane 128 may attach to the one or more flanges 120, which may be located between the first and second ends 118a, 118b of the transfer rod 118. Attaching the membrane 128 to the one or more flanges 120 provides a greater surface area for attachment and thus may increase the durability of the occlusion sensor system 200.

Attachment of the membrane 128 to the sidewalls 140 may position the transfer rod 118 to be adjacent tubing 124 when the infusion set is in use. To further increase the durability of pressure/occlusion sensor system 200, the area in which the membrane 128 contacts side walls 140 when attached can be extended vertically along the side walls 140. Also, as can be seen in FIG. 2, the area in which the membrane 128 contacts and attaches to the pump 114 can be extended further along surfaces of the pump body 114 other than the sidewalls 140. For example, the membrane 128 can have and extension or flange 128a so the membrane extends along the walls 140 and into a recess 144 or ledge in an inner surface of the walls (at the top, bottom or in between) to increase the surface area for engagement. One of skill in the art will appreciate that increasing the surface area used to attach the membrane 128 to the pump body 114 will likely increase the durability of the pressure/occlusion sensor system 200 and its ability to keep out liquids and other contaminants.

Figure 3:
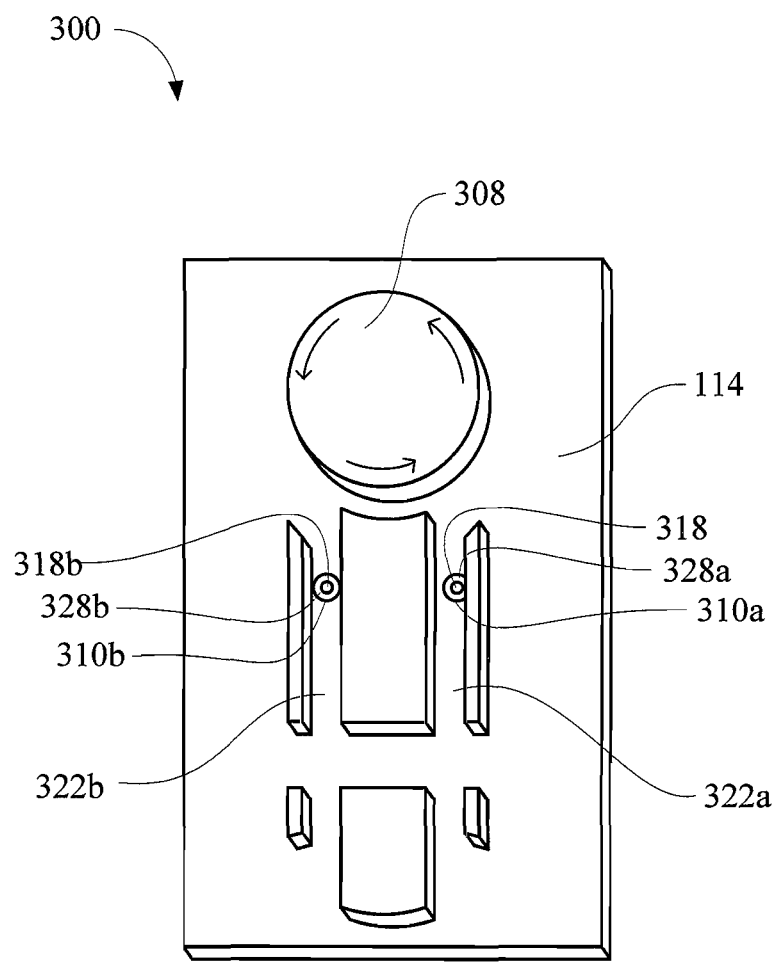
FIG. 3 shows a top view of a pump of an infusion set which can be used in accordance with the principles of the present invention.

Now turning to FIG. 3, a top view of a pump, generally indicated at 300, having a pump body 114 for receiving an infusion set is shown. According to one aspect of the invention the pump 300, may include at least two pressure/occlusion sensors 310a and 310b to allow for detection of occlusions, etc. that may occur upstream and/or downstream of the pumping mechanism 308, such as a pump rotor.

The pump mechanism 308 may be used to facilitate the flow of solutions through the tubing 124 (FIGS. 1-2) of an infusion set. The pump mechanism 308 pinches closed and compresses portions of the tubing to force fluid contained therein downstream. Such pumping mechanisms are well known in the art. It should be appreciated that pumps, other than rotary peristaltic pumps, including but not limited to linear, curvilinear and other pump configurations may be used according to principles of the present invention.

The pressure/occlusion sensors 310a, 310b may be made according to principles of the present invention. For example, the pressure/occlusion sensors 310a and 310b may be made in accordance with the configuration of the pressure/occlusion sensor system 100 shown in FIGS. 1 and 1A, or the pressure/occlusion sensor system 200 configuration shown in FIG. 2.

Tubing may be placed around the pump mechanism 308 and into the channels 322a, 322b. The transfer rods 318a, 318b may be positioned so as to contact the tubing when it is properly loaded in channels 322a, 322b. The membranes 328a, 328b may facilitate the positioning of the transfer rods 318a, 318b relative to the tubing. In other words, the transfer rods 318a, 318b may be held in place only by the membranes 328a, 328b. Thus, the membranes 328a, 328b may act as positioners, seals and microbial/contamination barriers between the outer and inner surfaces of the pump 300.

If an occlusion, partial occlusion or a lack of solution is present upstream of the pump 300, the pressure inside tubing located in the channel 322a will decrease causing the tubing to compress, i.e. reduce the radial diameter. Compression of the tubing will cause a reduced force to be exerted on the transfer rod 318a. The decrease in force may be communicated to the sensor via the transfer rod 318a and an alarm may be triggered to alert medical personnel of the occlusion if the drop in pressure is sufficient to indicate that action is needed.

If an occlusion or partial occlusion, etc., occurs downstream of pump 300, the pressure inside tubing located in channel 322b will increase causing the tubing to radially expand. A change in the force exerted on the transfer rod 318b due to the expansion of the tubing will be transferred to the sensor via the transfer rod, and may also trigger an alarm to medical personnel if the pressure exceeds a predetermined threshold.

Figure 4:
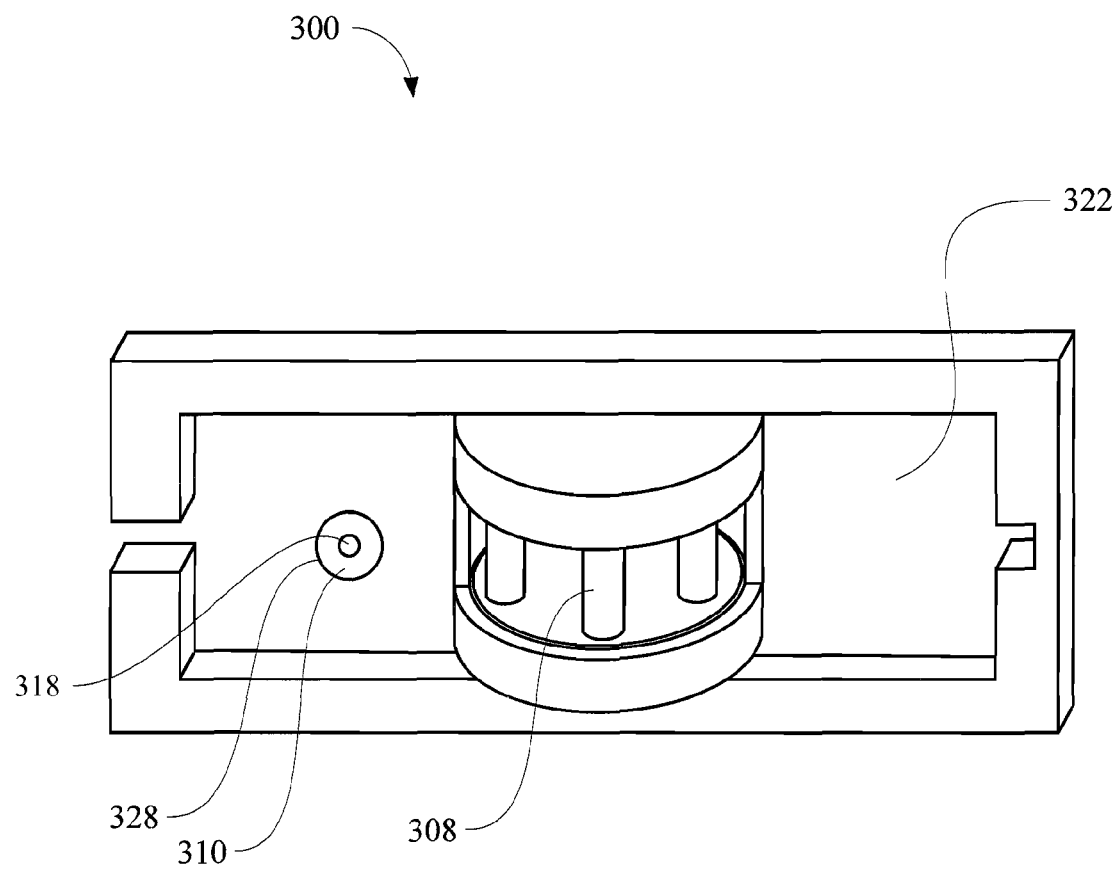
FIG. 4 shows a top view of another pump of an infusion set which can be used in accordance with the principles of the present invention.

It should be appreciated that a pump 300 may include only a single pressure/occlusion sensor 310, as shown in FIG. 4 which may be used to monitor pressure upstream or downstream from the pump mechanism 308. However, it is presently desirable to include at least two pressure/occlusion sensors positioned so as to be able to better detect an occlusion, partial occlusion, etc., that occurs either upstream or downstream of a pumping mechanism.

Figure 5:
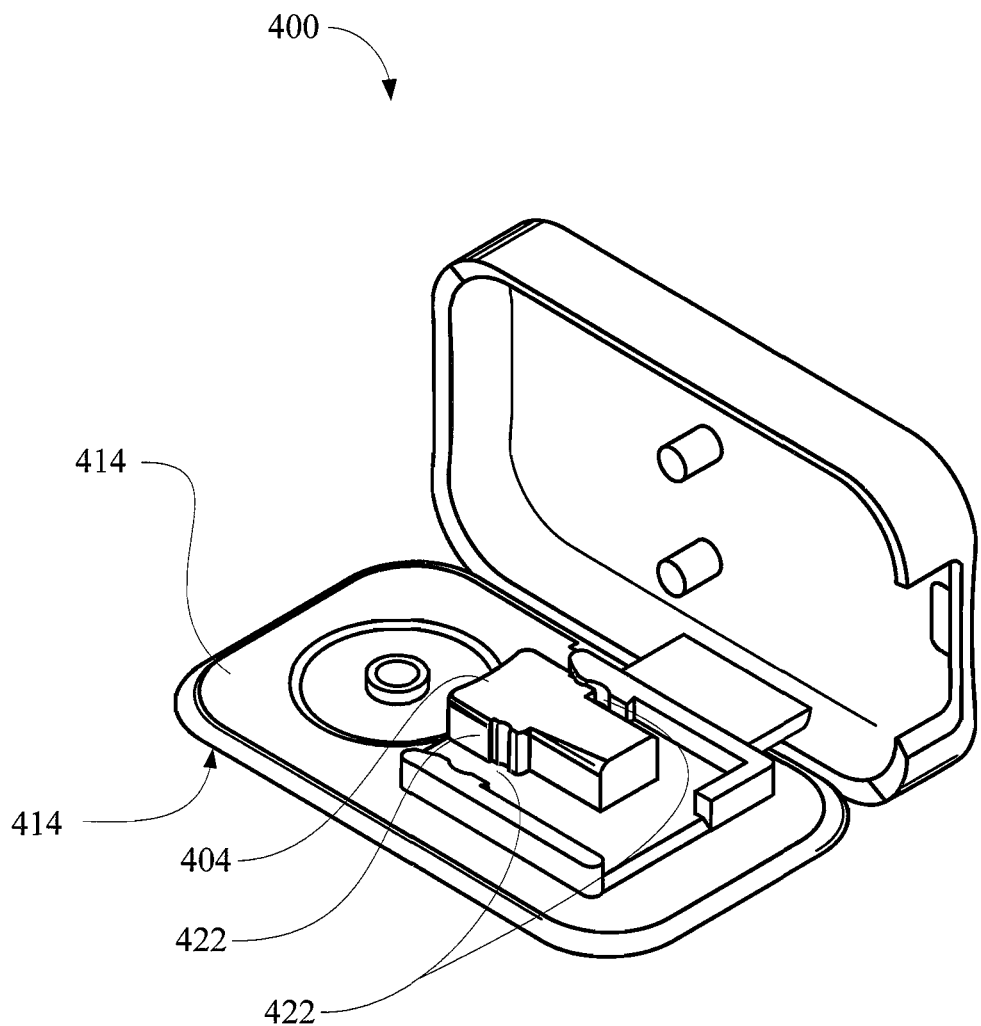
FIG. 5 shows a perspective view of a plate that can be attached to the pump of an infusion set which can be used according to principles of the present invention.

Now turning to FIG. 5, there is shown a perspective view of a plate or base, generally indicated at 400, that can be attached to or formed integrally with an infusion pump. The base 400 may include a mounting structure 404 which receives a cassette of an infusion set having a tubing segment (not shown). For example, the cassette may nest in the mounting structure 404, which helps to hold the cassette about the rotor (not shown) to facilitate the rotor driving solution through the tubing, such as enteral feeding solution, parenteral feeding solution, IV solution, etc.

Pressure/occlusion sensors 410 (which can be made as described above with respect to sensors 100, 200, 310) may be attached to the base 400 using a flexible, waterproof membrane (not shown) that acts as a microbial/contamination barrier and protects sensors located on the inner surface 414a of the plate 400 should solution leak from the infusion set or otherwise be spilled on the pump. The flexible, waterproof membrane may also aid in positioning the transfer rods of sensor system 410 such that a tubing segment of an infusion pump cassette 426 may be loaded into channels 422 of the base and held in direct contact with the transfer rods of pressure/occlusion sensor systems 410.

As discussed above, the transfer rods of pressure/occlusion sensor systems 410 are positioned so as to contact the tubing of the infusion set when in use. Furthermore, positioning of the transfer rods can be accomplished by overlay molding the flexible, waterproof membrane on the base 400 and the transfer rods.

While the discussion above has been principally in the context of an pressure/occlusion sensor which could be used in the administration of fluids to a patient, it will be understood that the occlusion sensor could be used in a variety of non-medical applications. Either way, the sensor system detects pressure change along the tubing of an infusion set and can thereby create a warning that pressure within the tubing has fallen below or exceeded a predetermined threshold. This could then be used to generate a warning signal or human perceptible signal, such as a light or audible alarm, and/or could be used to turn off the pump until the infusion set has been checked. Thus, proper pressures can be maintained by medical personnel with the pressure occlusion sensing system operating within a range of predetermined parameters.

It will be appreciated that the present invention can be used in a variety of apparatuses and methods. For example, a pressure sensor system in accordance with the present invention may include a sensor for determining pressure; a movable transfer rod disposed in communication with the sensor for applying force to the sensor, the transfer rod having a first end and a second end; and a flexible membrane connected to the transfer rod between the first end and the second end. The pressure system may be used in a pump: configured for pumping fluid through tubing, with the pump having a pump body and wherein the pressure sensor system is attached to a pump body; with the pump body having wall defining an opening and wherein the transfer rod is disposed in the opening and the flexible membrane is configured to form a seal in the opening between the transfer rod and the wall; where the flexible membrane is overlay molded on the pump body; further comprising a base disposed on the pump, the base being configured to receive a portion of an infusion set; with a base configured with a plurality walls defining at least one channel to receive an infusion set having a tubing segment and wherein the transfer rod is configured to be in direct contact with the tubing segment of the infusion set when mounted in the at least one channel; further comprising an infusion set having a cassette nestable on the base, the cassette having a tubing segment and wherein the transfer rod engages the tubing segment and moves responsive to radial expansions and contractions within the tubing segment; with an infusion set containing a solution selected from the group comprising enteral feeding solution, parenteral feeding solution, and IV solution; wherein the flexible membrane is configured to position the transfer rod both vertically and laterally relative to the pump body; wherein the flexible membrane is attached to the transfer rod and the pump body using overlay molding, the flexible membrane being formed from a waterproof material; wherein the pump has at least one recess adjacent the opening and wherein the flexible membrane is disposed in the at least one recess; and/or wherein the transfer rod comprises at least one flange and wherein the flexible membrane it attached to the at least one flange, or combinations thereof.

In accordance with one aspect of the invention, an infusion pump may include a pump body having a mounting plate for selectively receiving tubing of an infusion set; and a pressure sensor system comprising a sensor, a transfer rod for conveying pressure from a position adjacent the mounting plate to the sensor, and a flexible membrane attached to mounting plate and the transfer rod to form a seal around the transfer rod. The pump may also include: a transfer rod having a first end and a second end with a flexible membrane attached to the transfer rod between the first end and the second end; the flexible membrane positioned so that the membrane does not cover the first end or the second end of the transfer rod; the transfer rod having at least one flange, and wherein the flexible membrane is attached to the transfer rod via the at least one flange; a mounting plate is removably attachable to the infusion pump; a flexible membrane is attached to an extended surface of the mounting plate; the flexible membrane being attached to at least two non-parallel surfaces of the mounting plate; and/or the transfer rod being attached to the mounting plate by overlay molding the flexible membrane to the at least one flange of the transfer rod and to the mounting plate, or combinations thereof.

A method of manufacturing a pressure sensor system in accordance with the present invention may include the steps of: selecting a transfer rod having a first end and a second end; selecting a pump having an inner surface and an outer surface; connecting the transfer rod to the pump with a flexible membrane so as to form a contamination barrier between the inner and outer surfaces of the pump, the membrane attaching to the transfer rod between the first end and the second end; and the first end of the transfer rod being oriented to directly contact tubing of an infusion set, and wherein the second end of the transfer rod is disposed adjacent a pressure sensor. The method may also include: the transfer rod having at least one flange, and wherein the method further comprises attaching the flexible membrane to the at least one flange; the step of attaching the transfer rod to a mounting plate of the pump with the flexible membrane, wherein the mounting plate is removably attachable to the pump; the step of removably attaching a cassette of an infusion set having a tubing segment to the mounting plate, wherein removably attaching the mounting plate to the pump positions the tubing segment in direct contact with the transfer rod; and/or attaching the flexible membrane to the transfer rod and the mounting plate using overlay molding, or combinations thereof.

There is thus disclosed a pressure/occlusion sensor system and method of use. It will be appreciated that numerous changes may be made to the present invention without departing from the scope of the claims. The appended claims are intended to cover such modifications.

What is claimed is:

1. A pressure sensor system comprising:
a sensor for determining pressure;
a movable transfer rod disposed in communication with the sensor for applying force to the sensor, the transfer rod having a first end and a second end; and
a flexible membrane connected to the transfer rod between the first end and the second end;
wherein the pump is configured for pumping fluid through tubing, the pump having a pump body and wherein the pressure sensor system is attached to a pump body, the pump body having wall defining an opening and wherein the transfer rod is disposed in the opening and the flexible membrane is configured to form a seal in the opening between the transfer rod and the wall.

2. The pump according to claim 1, wherein the flexible membrane is overlay molded on the pump body.

3. A pump system comprising the pressure sensor according to claim 1, further comprising a base disposed on the pump, the base being configured to receive a portion of an infusion set.

4. The pump system according to claim 3, wherein the base is configured with a plurality walls defining at least one channel to receive an infusion set having a tubing segment and wherein the transfer rod is configured to be in direct contact with the tubing segment of the infusion set when mounted in the at least one channel.

5. A pump system according to claim 3, further comprising an infusion set having a cassette nestable on the base, the cassette having a tubing segment and wherein the transfer rod engages the tubing segment and moves responsive to radial expansions and contractions within the tubing segment.

6. The pump system according to claim 5, wherein the infusion set contains a solution selected from the group comprising enteral feeding solution, parenteral feeding solution, and IV solution.

7. The pump according to claim 1, wherein the flexible membrane is configured to position the transfer rod both vertically and laterally relative to the pump body.

8. The pump of claim 1, wherein the flexible membrane is attached to the transfer rod and the pump body using overlay molding, the flexible membrane being formed from a waterproof material.

9. The pump of claim 1, wherein the pump has at least one recess adjacent the opening and wherein the flexible membrane is disposed in the at least one recess.

10. The pressure sensor system of claim 1, wherein the transfer rod comprises at least one flange and wherein the flexible membrane it attached to the at least one flange.

11. An infusion pump comprising:
a pump body, the pump body having a mounting plate for selectively receiving tubing of an infusion set; and
a pressure sensor system comprising a sensor, a transfer rod for conveying pressure from a position adjacent the mounting plate to the sensor, and a flexible membrane attached to mounting plate and the transfer rod to form a seal around the transfer rod.

12. The infusion pump of claim 11, wherein the transfer rod comprises a first end and a second end and wherein the flexible membrane is attached to the transfer rod between the first end and the second end.

13. The infusion pump of claim 12, wherein the flexible membrane does not cover the first end or the second end of the transfer rod.

14. The infusion pump according to claim 11, wherein the transfer rod comprises at least one flange, and wherein the flexible membrane is attached to the transfer rod via the at least one flange.

15. The infusion pump according to claim 11, wherein the mounting plate is removably attachable to the infusion pump.

16. The infusion pump according to claim 11, wherein the flexible membrane is attached to an extended surface of the mounting plate.

17. The infusion pump according to claim 11, wherein the flexible membrane is attached to at least two non-parallel surfaces of the mounting plate.

18. The infusion pump according to claim 11, wherein the transfer rod is attached to the mounting plate by overlay molding the flexible membrane to the at least one flange of the transfer rod and to the mounting plate.

19. A method of manufacturing a pressure sensor system, the method comprising the steps of:
selecting a transfer rod having a first end and a second end;
selecting a pump having an inner surface and an outer surface;
connecting the transfer rod to the pump with a flexible membrane so as to form a contamination barrier between the inner and outer surfaces of the pump, the membrane attaching to the transfer rod between the first end and the second end; and
wherein the first end of the transfer rod is oriented to directly contact tubing of an infusion set, and wherein the second end of the transfer rod is disposed adjacent a pressure sensor.

20. The method according to claim 19, wherein the transfer rod comprises at least one flange, and wherein the method further comprises attaching the flexible membrane to the at least one flange.

21. The method according to claim 19, wherein the method further comprises the step of attaching the transfer rod to a mounting plate of the pump with the flexible membrane, wherein the mounting plate is removably attachable to the pump.

22. The method according to claim 21, further comprising the step of removably attaching a cassette of an infusion set having a tubing segment to the mounting plate, wherein removably attaching the mounting plate to the pump positions the tubing segment in direct contact with the transfer rod.

23. The method according to claim 21, wherein the flexible membrane is attached to the transfer rod and the mounting plate using overlay molding.

* * * * *